United States Patent [19]

Simon et al.

[11] 4,221,794
[45] Sep. 9, 1980

[54] METHOD OF IMPARTING IMMUNOMODULATING AND ANTIVIRAL ACTIVITY

[75] Inventors: Lionel N. Simon, Santa Ana, Calif.; John W. Hadden, New York, N.Y.

[73] Assignees: Newport Pharmaceuticals Intern., Inc., Calif.; Sloan-Kettering Instit. for Cancer Res., New York, N.Y.

[21] Appl. No.: 50,785

[22] Filed: Jun. 21, 1979

Related U.S. Application Data

[62] Division of Ser. No. 942,802, Sep. 15, 1978.

[51] Int. Cl.³ ............................................. A01N 43/90
[52] U.S. Cl. ................................... 424/253; 544/277; 544/265
[58] Field of Search ......................... 544/277; 424/253

[56] References Cited

PUBLICATIONS

Schaeffer et al., J. Med. Chem. 17, pp. 6–8 (1974).
Schaeffer et al., J. Med. Chem. 15, pp. 456–458 (1972).
Schaeffer et al., Biochemistry 4, pp. 71–76 (1965).

*Primary Examiner*—Nicholas S. Rizzo
*Attorney, Agent, or Firm*—Cushman, Darby & Cushman

[57] ABSTRACT

Compounds of the formula

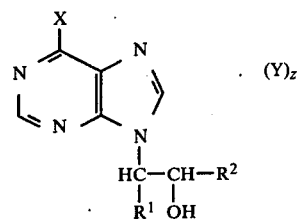

where X is OH, $NH_2$, SH, OR or SR (where R is alkyl of 1 to 4 carbon atoms or benzyl), $R^1$ is H or alkyl of 1 to 8 carbon atoms, $R^2$ is H or methyl, Y is the salt of an amine of the formula

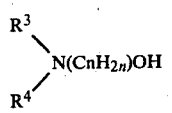

where $R^3$ and $R^4$ are lower alkyl, e.g., 1 to 4 carbon atoms and n is an integer of 2 to 4 with p-acetamidobenzoic acid and where z is a number from 0 to 10 are useful as immunomodulators, as antiviral agents and in specific cases have anti-leukemic activity. The compounds and compositions where z is 1 to 10 are novel per se. When $R^2$ is H the presence of Y enhances the immunoregulatory activity and the antiviral activity. If X is the $NH_2$ there is immunoinhibitory activity but no immunostimulatory (immunopotentiatory) activity.

93 Claims, No Drawings

METHOD OF IMPARTING IMMUNOMODULATING AND ANTIVIRAL ACTIVITY

This is a division of application Ser. No. 942,802, filed Sept. 15, 1978.

SUMMARY OF THE INVENTION

The present invention is based on the discovery that compounds of the formula

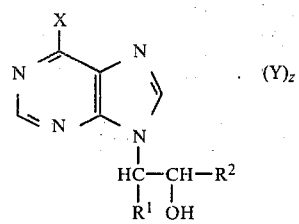

where X is OH, $NH_2$, SH, OR or SR where R is alkyl of 1 to 4 carbon atoms or benzyl, $R^1$ is H or alkyl of 1 to 8 carbon atoms, $R^2$ is H or methyl, Y is the salt of an amine of the formula

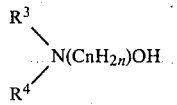

where $R^3$ and $R^4$ are lower alkyl, e.g., 1 to 4 carbon atoms and n is an integer of 2 to 4 with p-acetamidobenzoic acid and where z is a number from 0 to 10 are useful as immunomodulators, as antiviral agents and in specific cases have anti-leukemic activity. The compounds and compositions where z is 1 to 10 are novel per se. When $R^2$ is H the presence of Y enhances the immunoregulatory activity and the antiviral activity. If X is the $NH_2$ there is immunoinhibitory activity but no immunostimulatory (immunopotentiatory) activity.

Immunoregulatory activity appears to increase with increasing chain length for $R^1$, at least from methyl through hexyl. Preferably $R^1$ is n-alkyl, i.e., methyl, ethyl, n-propyl, n-butyl, n-amyl, n-hexyl, n-heptyl or n-octyl. $R^2$ is preferably methyl. R can be methyl, ethyl, n-propyl, n-butyl, isopropyl, etc. When X is $NH_2$ the compound can be present as the free base or as the salt with a non-toxic acid, i.e., pharmaceutically acceptable acid, e.g., hydrochloric acid, hydrobromic acid, sulfuric acid, phosphonic acid, citric acid, lactic acids, tartaric acid, salicylic acid, acetyl salicyclic acid, acetic acid, propionic acid, p-toluene sulfonic acid, methane sulfonic acid, maleic acid, succinic acid, malonic acid, adipic acid.

A preferred class of amines to form the salt with para acetamidobenzoic acid has the formula

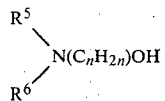

where $R^5$ and $R^6$ are lower alkyl, e.g., methyl, ethyl, propyl, isopropyl or butyl and n is an integer of 2 to 4. Typical examples of such amines include dimethylamino ethanol, dimethylamino isopropanol, diethylamino ethanol, diethylamino isobutanol, diethylamino isopropanol, methyl ethyl amino ethanol, diisobutylamino-N-butanol, dimethylamino propanol, dimethylamino-N-butanol, diisobutylamino ethanol, dimethylamino butanol, dibutylamino-N-butanol, dibutylamino ethanol, dipropylamino ethanol and diisopropylamino ethanol. The presently preferred amine is dimethylamino isopropanol. When Y is present, i.e., z is 1 to 10, preferably z is 3. However, z can also be 1, 2, 4, 5, 6, 7, 8, 9 or 10.

While there are preferably used the compounds where Y is the salt of the amine

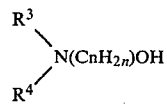

with p-acetamidobenzoic acid there can also be used salts of the formula $Y^1$ wherein the amine is as just defined the acid is a pharmaceutically acceptable acid other than p-acetamidobenzoic acid, e.g., hydrochloric acid, sulfuric acid, hydrobromic acid, phosphoric acid, acetic acid, propionic acid, malonic acid, lactic acid, citric acid, tartaric acid, p-toluene sulfonic acid, adipic acid, maleic acid, succinic acid, methane sulfonic acid, salicylic acid, acetyl salicylic acid.

In describing the compounds below, when Y is present the abbreviation DIP.PAcBA stands for dimethylamino-2-propanol-p-acetamido benzoate. Unless a number in parentheses, e.g. (10), follows this abbreviation, then Y is 3. If a number in parentheses follows the abbreviation DIP.PAcBA there the number indicates the number of moles of Y groups present to 1 mole of the 9-(hydroxyalkyl)purine.

In Table 1 below the compounds are believed to be pure except for compound 15443 which is believed to also contain a salt in addition to the compound of the invention.

An immunomodulator is a compound which regulates the immune response. Thus it covers both immunostimulation (immunopotentiation) and immunoinhibition. Immunostimulation, of course, is useful in building up immunity. Immunoinhibition also has utility in a number of areas. For example, it is useful in organ transplants, e.g., kidney or heart transplants, to prevent rejection.

In the tables showing the immunopotentiating properties of the compounds, a plus or a minus (−) indicates immunostimulating or immunoinhibiting properties. Respectively the number 0 indicates the compound had neither immunopotentiating activity of immunoinhibiting activity.

There are included in some of the tables several compounds wherein X is not within that claimed. These non-claimed compounds as a rule have relatively low activities and are included to illustrate the fact that the X group can have a significant effect on the properties of the compounds.

A mitogen is a substance which induces cell proliferation, as occurs during immunization.

Table 1 (excluding compounds 15427 and 15423) shows compounds useful in the invention.

The synthetic procedures A through L mentioned in Table 1 are described in more detail subsequently.

The compositions of the invention are useful in treating mammals (and cells of mammals) including humans, swine, dogs, cats, cattle, horses, sheep, goats, mice, rabbits, rats, guinea pigs, hamsters, monkeys, etc.

Unless otherwise indicated, all parts and percentages are by weight.

All temperatures are in degrees centigrade unless otherwise indicated.

The compositions can comprise, consist essentially of or consist of the materials set forth and the processes can comprise, consist essentially of or consist of the steps set forth with such materials.

The compositions can be administered to the mammals by conventional techniques, e.g., orally, nasally, rectally, vaginally, enterally or parenterally. They can be employed as injectable solutions, e.g., in water, or as tablets, pills, capsules, etc.

Other compounds within the invention are set forth in Table 1a below wherein the basic formula is the same as that in Table 1. In Tables 1 and 1a, the alkyl groups for $R^1$ are all n-alkyl.

Table 1a

| $R^1$ | $R^2$ | X | Y |
|---|---|---|---|
| $C_6H_{13}$ | $CH_3$ | OH | DIP . PAcBA(10) |
| $C_6H_{13}$ | $CH_3$ | OH | DIP . PAcBA(1) |
| H | $CH_3$ | OH | DIP . PAcBA(10) |
| H | $CH_3$ | OH | DIP . PAcBA(1) |
| $CH_3$ | $CH_3$ | OH | — |
| $CH_3$ | $CH_3$ | OH | DIP . PAcBA |
| $C_2H_5$ | H | OH | DIP . PAcBA |
| $C_2H_5$ | H | OH | — |
| $C_3H_7$ | H | OH | — |
| $C_3H_7$ | H | OH | DIP . PAcBA |
| $C_2H_5$ | $CH_3$ | OH | — |
| $C_2H_5$ | $CH_3$ | OH | DIP . PAcBA |
| $C_2H_7$ | $CH_3$ | OH | — |
| $C_3H_7$ | $CH_3$ | OH | DIP . PAcBA |
| $C_4H_9$ | H | OH | — |
| $C_4H_9$ | H | OH | DIP . PAcBA |
| $C_4H_9$ | $CH_3$ | OH | — |
| $C_4H_9$ | $CH_3$ | OH | DIP . PAcBA |
| $C_5H_{11}$ | H | OH | — |

Table 1

SUMMARY OF CHEMICAL PROPERTIES OF 9-(HYDROXYALKYL) PURINES

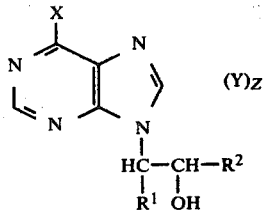

| No. | $R^1$ | $R^2$ | X | Y | Synthetic Method | M.Pt. °C. | λMax. | λMin. | Con $10^{-3}$ | pH | C | H | N |
|---|---|---|---|---|---|---|---|---|---|---|---|---|---|
| 15425 | H | H | OH | — | D | 274° | 250 | 222.5 | 11.93 | 7 | | | |
| | | | | | | | 250 | 219 | 11.0 | 1 | | | |
| | | | | | | | 254 | 221.5 | 12.53 | 10 | | | |
| 15428 | H | H | OH | DIP . PAcBA | L | | 323 | 251 | 23.0 | 7 | | | |
| 15435 | H | H | SH | — | C | 278–80 | 323 | 252 | 19.9 | 1 | | | |
| | | | | | | | 323 | 251 | 19.9 | 10 | | | |
| 15437 | H | H | SH | DIP . PAcBA | L | | 250 | 223.5 | 11.0 | 7 | | | |
| 15446 | H | $CH_3$ | OH | — | A | 244–5 | 250 | 220 | 10.6 | 1 | | | |
| | | | | | | | 254 | 223.5 | 12.1 | 10 | | | |
| 15447 | H | $CH_3$ | OH | DIP . PAcBA | L | | 261 | 228 | 15.8 | 7 | Cal 49.73 | 5.74 | 36.25 |
| 15431 | H | $CH_3$ | $NH_2$ | — | B | 188° | 259 | 231 | 15.4 | 1 | FD 49.56 | 5.62 | 36.22 |
| | | | | | | | 261 | 225 | 15.7 | 10 | | | |
| 15432 | H | $CH_3$ | $NH_2$ | DIP . PAcBA | L | | 276 | 237 | 10.9 | 7 | Cal 31.60 | 2.98 | 18.43 |
| 15427 | $CH_3$ | H | I | — | E | 178° | 276 | 237 | 10.9 | 1 | FD 31.53 | 2.96 | 18.18 |
| | | | | | | | 276 | 237 | 10.9 | 10 | | | |
| | | | | | | | 265 | 228 | 9.1 | 7 | Cal 45.20 | 4.26 | 26.36 |
| 15423 | $CH_3$ | H | Cl | — | F | 200–204 | 265 | 228 | 9.1 | 1 | FD 45.11 | 4.27 | 26.25 |
| | | | | | | | 265 | 228 | 9.1 | 10 | | | |
| | | | | | | | 261.5 | 228 | 13.56 | 7 | | | |
| 15433 | $CH_3$ | H | $NH_2$ | — | G | 215–16 | 259 | 231 | 13.26 | 1 | | | |
| | | | | | | | 261 | 224.5 | 13.80 | 10 | | | |
| 15434 | $CH_3$ | H | $NH_2$ | DIP . PAcBA | L | | 250 | 223 | 7.52 | 7 | | | |
| 15443 | $CH_3$ | H | OH | — | H | 198–199 | 250 | 218 | 6.91 | 1 | | | |
| | | | | | | | 255 | 225.5 | 7.91 | 10 | | | |
| 15444 | $CH_3$ | H | OH | DIP . PAcBA | L | | 250 | 224 | 11.09 | 7 | Cal 59.07 | 7.65 | 21.16 |
| 15417 | $C_6H_{13}$ | H | OH | — | I | 226° C. | 250 | 220 | 10.37 | 1 | FD 59.01 | 7.55 | 21.24 |
| | | | | | | | 255 | 223 | 11.96 | 10 | | | |
| 15418 | $C_6H_{13}$ | H | OH | DIP . PAcBA | L | | 250 | 224 | 12.1 | 7 | Cal 60.41 | 7.97 | 20.13 |
| 15392 | $C_6H_{13}$ | $CH_3$ | OH | — | J | 202° C. | 248 | 222 | 13.3 | 1 | FD 60.47 | 7.86 | 20.08 |
| | | | | | | | 254 | 220 | 14.1 | 10 | | | |
| 15410 | $C_6H_{13}$ | $CH_3$ | OH | DIP . PAcBA | L | | 261 | 230 | 9.77 | 7 | Cal 58.58 | 7.71 | 22.32 |
| 15426 | $C_6H_{13}$ | $CH_3$ | $NH_2$ | HCl Salt | K | 176°–9° C. | 259 | 233 | 9.60 | 1 | FD 53.56 | 7.67 | 22.24 |
| | | | | | | | 261 | 235 | 9.77 | 10 | | | |

Table 1a-continued

| R¹ | R² | COMPOUND X | Y |
|---|---|---|---|
| C5H11 | H | OH | DIP . PAcBA |
| C5H11 | CH3 | OH | DIP . PAcBA |
| C5H11 | CH3 | OH | — |
| C7H15 | H | OH | — |
| C7H15 | H | OH | DIP . PAcBA |
| C7H15 | CH3 | OH | — |
| C7H15 | CH3 | OH | DIP . PAcBA |
| C8H17 | H | OH | — |
| C8H17 | H | OH | DIP . PAcBA |
| C8H17 | CH3 | OH | — |
| C8H17 | CH3 | OH | DIP . PAcBA |
| C6H13 | CH3 | OCH3 | — |
| C6H13 | CH3 | OCH3 | DIP . PAcBA |
| C6H13 | H | OCH3 | DIP. PAcBA |
| C6H13 | H | OCH3 | — |
| CH3 | H | OCH3 | — |
| CH3 | H | OCH3 | DIP . PAcBA |
| H | H | OCH3 | — |
| H | H | OCH3 | DIP . PacBA |
| H | CH3 | OCH3 | DIP . PAcBA |
| H | CH3 | OCH3 | — |
| C6H13 | CH3 | OC2H5 | — |
| C6H13 | CH3 | OC2H5 | DIP . PAcBA |
| C6H13 | H | OC2H5 | DIP . PAcBA |
| C6H13 | H | OC2H5 | — |
| C6H13 | CH3 | OC3H7 | — |
| C6H13 | CH3 | OC3H7 | DIP . PAcBA |
| CH3 | H | OC3H7 | DIP . PAcBA |
| CH3 | H | OC3H7 | — |
| H | H | OC3H7 | DIP . PAcBA |
| H | CH3 | OC3H7 | DIP . PAcBA |
| C6H13 | CH3 | OC4H9 | — |
| C6H13 | H | OC4H9 | — |
| C6H13 | H | OC4H9 | DIP . PAcBA |
| H | H | OC4H9 | — |
| H | H | OC4H9 | DIP . PAcBA |
| H | CH3 | OC4H9 | — |
| H | CH3 | OC4H9 | DIP . PAcBA |
| CH3 | CH3 | OC4H9 | — |
| CH3 | CH3 | OC4H9 | DIP . PAcBA |
| CH3 | H | OC4H9 | — |
| CH3 | H | OC4H9 | DIP . PAcBA |
| C6H13 | CH3 | SCH3 | — |
| C6H13 | CH3 | SCH3 | DIP . PAcBA |
| C6H13 | H | SCH3 | — |
| C6H13 | H | SCH3 | DIP . PAcBA |
| CH3 | CH3 | SCH3 | — |
| CH3 | CH3 | SCH3 | DIP . PAcBA |
| CH3 | H | SCH3 | — |
| CH3 | H | SCH3 | DIP . PAcBA |
| H | H | SCH3 | — |
| H | H | SCH3 | DIP . PAcBA |
| H | CH3 | SCH3 | DIP . PAcBA |
| H | CH3 | SCH3 | — |
| C6H13 | CH3 | SC4H | — |
| C6H13 | CH3 | SC4H9 | DIP . PAcBA |
| C6H13 | H | SC4H9 | DIP . PAcBA |
| C6H13 | H | SC4H9 | — |
| CH3 | H | SC4H9 | — |
| CH3 | H | SC4H9 | DIP . PAcBA |
| H | H | SC4H9 | — |
| H | H | SC4H9 | DIP . PAcBA |
| H | CH3 | SC4H9 | DIP . PAcBA |
| H | CH3 | OH | DIP . PAcBA(10) |
| H | CH3 | OH | DIP . PAcBA(1) |
| C6H13 | H | O-benzyl | — |
| C6H13 | H | O-benzyl | DIP . PAcBA |
| C6H13 | CH3 | O-benzyl | — |
| C6H13 | CH3 | O-benzyl | DIP . PAcBA |
| C6H13 | CH3 | S-benzyl | — |
| C6H13 | CH3 | S-benzyl | DIP . PAcBA |
| C6H13 | H | S-benzyl | — |
| C6H13 | H | S-benzyl | DIP . PAcBA |

DESCRIPTION OF THE PREFERRED EMBODIMENTS

Method A 9-(2-HYDROXY-1-PROPYL)HYPOXANTHINE (NPT 15446)

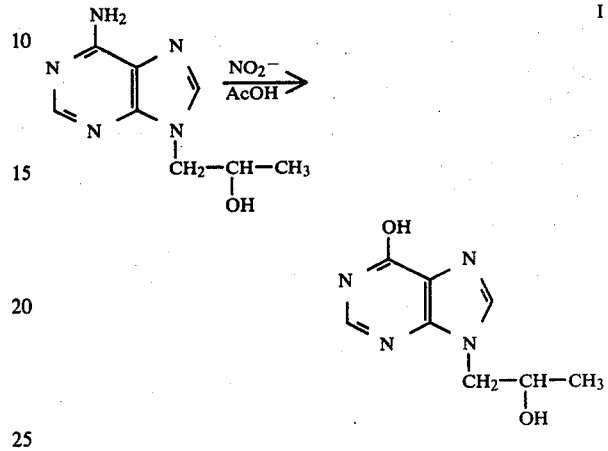

9-2-Hydroxy-1-propyl)adenine (I, 4.0 g, 20.7 mmol) was suspened in 50% acetic acid (20 ml) and sodium nitrite (4 g, 58 mmol), was slowly added. The mixture was stirred at 25° for 3 hr. The resulting solution was evaporated to dryness and isopropanol added; this operation was repeated once. The solid residue was boiled in isopropanol and filtered. The filtrate was evaporated and crystallized by addition of acetone. Recrystallization was made from iso-propanol/methanol (98:2); a colorless crystalline product was obtained. Yield 3.3 g (82%) M.P. 244°–250° uv ($H_2O$; pH 5.5) λmax 250 nm

Method B 9-(2-HYDROXY-1-PROPYL)-6-CHLOROPURINE

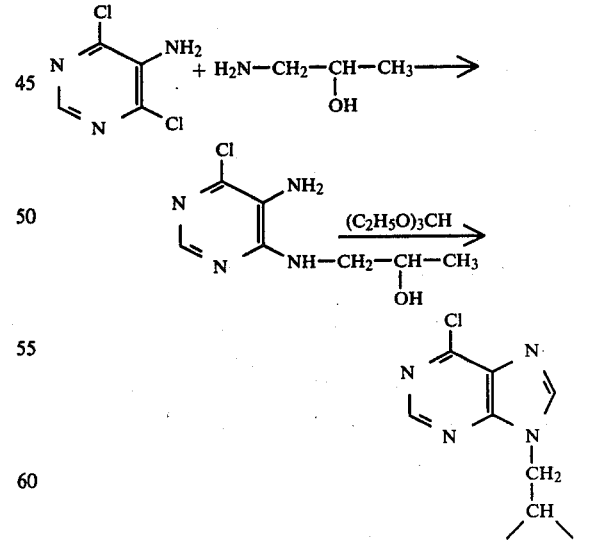

There were employed the methods of Schaeffer, H. J., Vogel, D. and Vince, R., J. Med. Chem. 8, 502 (1965); and Schaeffer, H. J. and Vince, R., J. Med. Chem. 10, 689 (1967).

A solution of 5-amino-4,6-dichloropyrimidine (I, 20 g, 0.12 mole) in 11% ethanolic solution of isopropanolamine (200 ml) was refluxed for 8 hr. The reaction mixture was evaporated to a syrup, ethanol added and evaporated again; this operation was repeated once. The resulting syrup was poured into water (300 ml) giving a crystalline mass. It was collected by filtration, washed with water and dried to give 19 g of crude 9-(2-hydroxy-1-propylamino)5-amino-6 chloropyrimidine (II).

The crude compound II was suspended in triethylorthoformate (120 ml) to which ethanesulfonic acid (5 drops) was added. After 15 min. all the solid dissolved and the solution was kept at 25° overnight. Evaporation in vacuo gave a thick syrup which was submitted to high vacuo evaporation to remove the excess of isopropanolamine. Upon crystallization with xylene, 5 g of crude material was obtained.

Method B

9-(2-HYDROXY-1-PROPYL)ADENINE (NPT 15431)

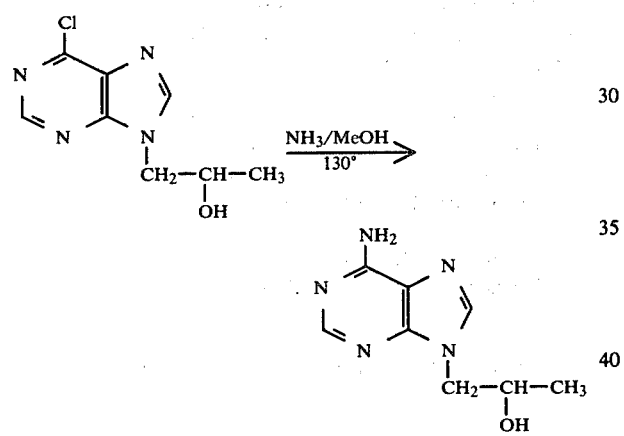

9-(2-Hydroxy-1-propyl)-6-chloropurine (I, 9 g, 42.5 mmol) was dissolved in saturated methanolic ammonia and ammonium chloride (50 mg). The mixture was heated at 130° in a bomb for 6 hr. The resulting solution was evaporated to dryness and recrystallized from ethanol/acetone. Yield=6.68 g of a colorless crystalline product (81%) mp 193°-194° uv (H$_2$O; pH 5.5) λmax 260 nm TLC in CHl$_3$:MeOH (5:1) R$_f$ 0.44

Anal. Calc. for C$_8$H$_{11}$N$_5$O: C, 49.73; H, 5.74; N, 36.25; Found: C, 49.56, H, 5.62; N, 36.22.

Method C

9-(1-HYDROXYETHYL)-6-MERCAPTOPURINE (NPT 15435)

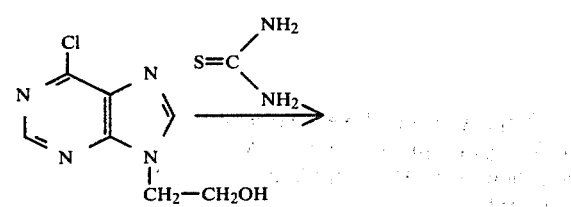

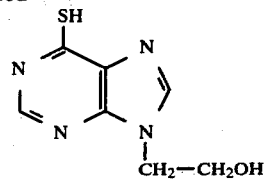

There was employed the method of Schaeffer and Bhargava, Biochemistry 4, 71 (1965).

9-(1-Hydroxyethyl)-6-chloropurine (I, 2 g, 0.01 mol) and thiourea (0.76 g; 0.01 mol) were dissolved in ethanol (15 ml) and refluxed for 30 min. The resulting precipitate was collected by filtration and suspended in water to form a slurry. Neutralization with sodium acetate gave colorless crystals. Yield 1.5 g (76%).

M.P. 278°-280°; uv (H$_2$O, pH 5.5) λmax 320, 230 nm.

Method D

9-HYDROXYETHYL HYPOXANTHINE (NPT 15425)

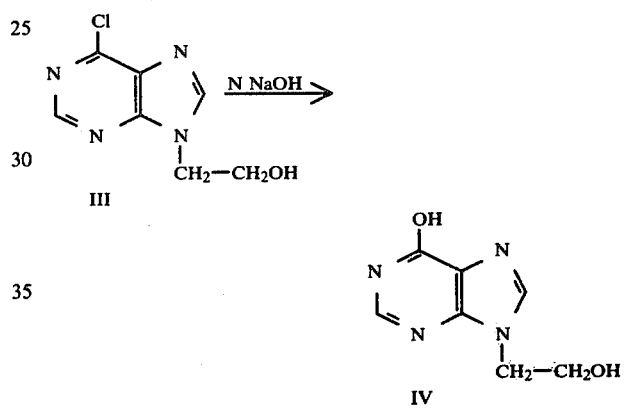

There was used the method of Schaeffer, H. J. and Bhargava, P. S., Biochemistry 4, 71 (1965).

6-Chloro-9-hydroxyethyl purine, III (4 g), was added slowly to warm N NaOH (30 ml) and refluxed for 2 hr. The reaction is cooled in ice and neutralized with glacial acetic acid. After filtration, portions of unreacted III are removed. The product is recrystallized from methanol and washed with acetone. Colorless crystals. Yield, 1 g. (28%); mp. 274°; uv (H$_2$O, pH 5.5), λmax 250 nm.

Method E

9-(1-HYDROXYL-2-PROPYL)-6-IODOPURINE (NPT 15427)

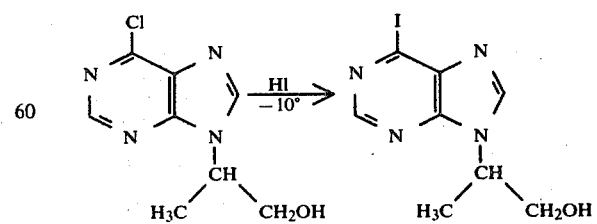

9-(1-Hydroxy-2-propyl)-6-chloropurine (I, 1.5 g, 7 mmol) was added to hydroiodic acid (15 ml) at −10° with stirring for 45 min. The precipitate was filtered, neutralized with anhydrous sodium acetate at 5°, and washed with a little cold water (3 times). Recrystallization from ethanol/H₂O, gave colorless crystals. Yield=0.9 g (42%) mp=193°-194° uv λmax 276 nm (H₂O, pH 5.5).

Anal. Calc. for C₈H₉N₄OI MW=304.1: C, 31.60; H, 2.98; N, 18.43; I, 41.73. Found: C, 31.53; H, 2.96; N, 18.18; I, 41.70.

Method F

9-(1-HYDROXY-2-PROPANE)-6-CHLOROPURINE (NPT 15423)

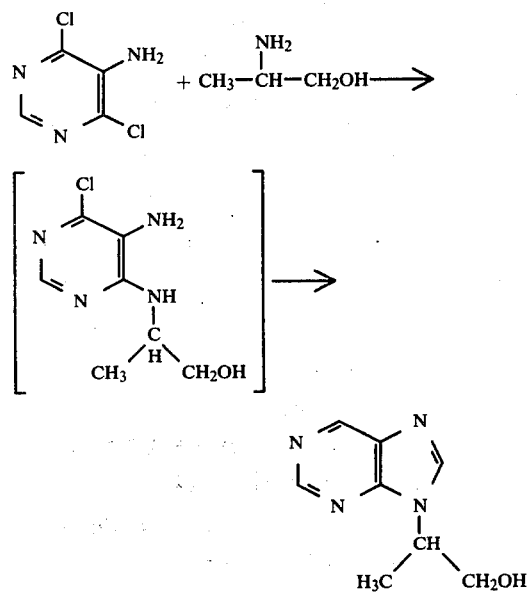

There was used the method of Schaeffer, H. J. and Schwender, C. F., J. Med. Chem. 17, 6 (1974).

A solution of 5-amino-4,6-dichloropyrimidine (I, 6.56 g 40 mmol) and 2-amino-1-propanol (II, 3.3 g, 44 mmol) was refluxed in n-pentanol (288 ml) and tert-butylamine (96 ml) for 45 hr. under N₂ atmosphere. The solution was evaporated to a syrup and ethanol added 4 times and evaporated. The resulting syrup was suspended in triethylorthoformate (150 ml) and ethanesulfonic acid (10 drops). The suspension was vigorously stirred overnight, then evaporated to dryness, ethanol added and this operation repeated three times. Crystallization of colorless product occurs during evaporation. The crystals were filtered, and the filtrate was evaporated, ethanol added and this operation repeated three times to give a crude material (3.6 g).

Recrystallized from 98% aqueous ethanol. uv (H₂O, pH 5.5) λmax 265 nm; mp 201°-203°; yield 2.79 (32%).

Anal. C₈H₉N₄OCl. Calc. C, 45.20; H, 4.26; N, 26.36; Cl, 16.68. Found: C, 45.11; H, 4.27; N, 26.25; Cl, 16.71.

Method G

9-(1-HYDROXY-2-PROPYL)ADENINE (NPT 15433)

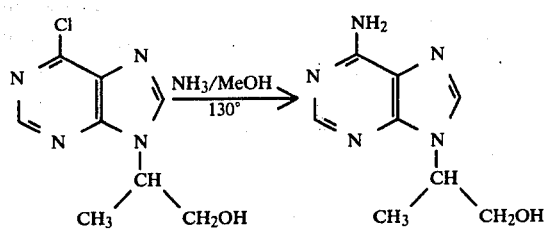

There was used the procedure of Schaeffer, H. and Schwender, C., J. Pharm. Sci., 60, 1204 (1971). Also Schaeffer et al., J. Med. Chem. 15, 456 (1972).

9-(1-Hydroxy-2-propyl)-6-chloropurine (I, 2.0 g, 9.4 mmol) was suspended in methanol/ammonia (30 ml) and ammonium chloride (50 mg) added as a catalyst and the mixture heated at 130° for 4.5 hr; the solution was evaporated to dryness. Recrystallization from ethanol of the obtained crude product gave colorless needles. Yield=1.15 g (63%) mp=215°-216° uv (H₂O, pH 5.5) λmax, 260 nm.

Method H

9-(1-HYDROXY-2-PROPYL)HYPOXANTHINE (NPT 15443)

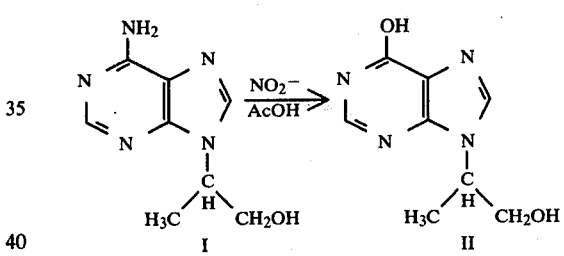

9-(1-Hydroxy-2-propyl)adenine (I, 4 g, 21 mmol) was dissolved in 50% acetic acid (20 ml), sodium nitrite (4 g, 58 mmol) added and the mixture stirred at 25° for 3½ hr. The solution was evaporated to dryness twice with isopropanol. The residue was taken up in isopropanol and filtered, the precipitate discarded, and the filtrate evaporated to form a gel which, upon the addition of acetone, solidified. Yield=3.65 (90%) of colorless crystals. Recrystallized from isopropanol/methanol (98:2). mp=202°-207° TLC in CHCl₃:MeOH (5:1) 1 spot R$_f$—0.30 uv (H₂O, pH 5.5)=λmax 250 nm.

Method I

COMPOUND NPT 15417

There was used the procedure of Schaeffer et al, Journal of Pharmaceutical Sciences 16:1204-1210, Method F.

The product is compound XL in Table III of Schaeffer et al.

Method J

ERYTHRO-9-(2-HYDROXY-3-NONYL)HYPOXANTHINE (NPT 15392)

An outline of the synthetic sequence for the preparation of erythro-9-(2-hydroxy-3-nonyl)hypoxanthine (Nonylhypoxanthine, VIII) is shown in Flow Charts 1 and 2. The improvements over the procedure of H. J. Schaeffer and C. F. Schwender, J. Med. Chem., 17, 6 (1974) in the reaction sequence leading to the erythro-9-(2-hydroxy-3-nonyl)-6-chloropurine (VII) are indicated. The last step, the hydrolysis of the 6-chloropurine derivative (VII), to yield nonylhypoxanthine (VIII) is an adaptation of the method reported by A. Giner-Sorolla, C. Gryte, A. Bendich and G. B. Brown, J. Org. Chem. 34, 2157 (1969) for the hydrolysis of halogenopurines.

The alternate route, i.e., the nitrosation of erythro-9-(2-hydroxy-3-nonyl)adenin (EHNA) (IX), to yield Nonylhypoxanthine (VIII) (shown on Flow Chart 2) consists of the previous conversion by ammonolysis of the chloro derivative (VII) into the aminopurine (IX, EHNA) followed by its nitrosation to yield Nonylhypoxanthine (VIII).

Flow Chart 1

OUTLINE OF THE SYNTHESIS OF ERYTHRO-9-(2-HYDROXY-3-NONYL)HYPOXANTHINE (VIII)

Step 1

ACETAMIDONONAN-2-ONE (II)

Acylation of 2-amino octanoic acid

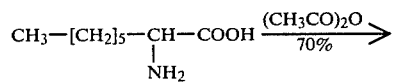

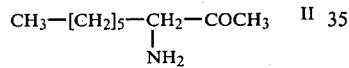

Step 2

ACETAMIDONONAN-2-ONE HYDROCHLORIDE (III)

Formation of the acetamidononan-2-one hydrochloride

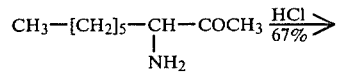

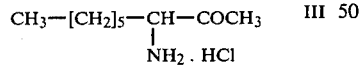

Step 3

ERYTHRO-3-AMINO-2-NONANOL (IV)

Reduction of the acetamidononan-2-one hydrochloride

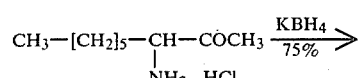

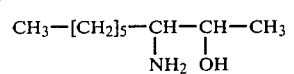

(Figures below the arrow refer to % yield.)

Step 4

ERYTHRO-5-AMINO-4-CHLORO-6-(2-HYDROXY-3-NONYLAMINO)PYRIMIDINE (VI)

Condensation of erythro-3-amino-2-nonanol with 5 amino-4,6-dichloropyrimidine

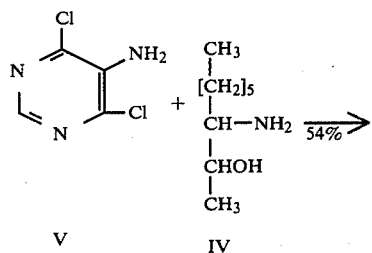

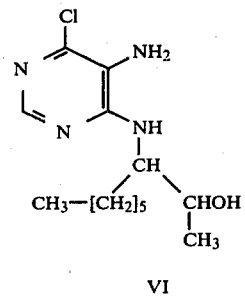

Step 5

ERYTHRO-9-(2-HYDROXY-3-NONYL)-6-CHLOROPURINE (VII)

Ring closure of erythro-5-amino-4-chloro-6-(2-hydroxy-3-nonylamino)pyrimidine (V)

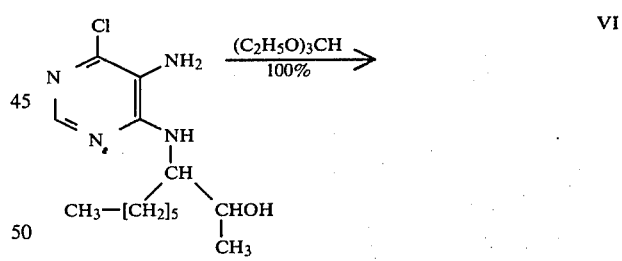

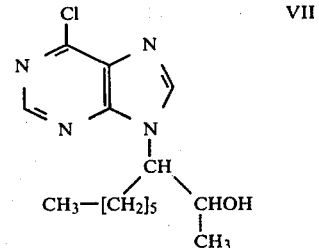

Step 6

ERYTHRO-9-(2-HYDROXY-3-NONYL)HYPOXANTHINE (VIII)

(By hydrolysis of the 6-chloropurine derivative)

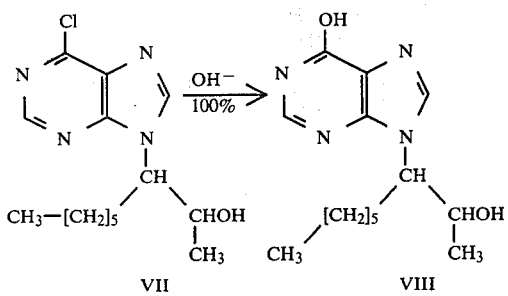

Flow Chart 2
ALTERNATIVE ROUTE FOR THE PREPARATION OF ERYTHRO-9-(2-HYDROXY-3-NONYL HYPOXANTHINE (VIII)

Step 1a
ERYTHRO-9-(2-HYDROXY-3-NONYL)ADENINE (IX)

Ammonolysis of erythro-9-(2-hydroxy-3-nonyl)-6-chloropurine (VII)

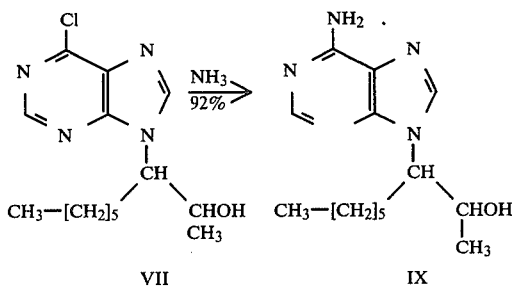

Step 2b
ERYTHRO-9-(2-HYDROXY-3-NONYL)HYPOX- ANTHINE (VIII)

Nitrosation of erythro-9-(2-hydroxy-3-nonyl)adenine (IX)

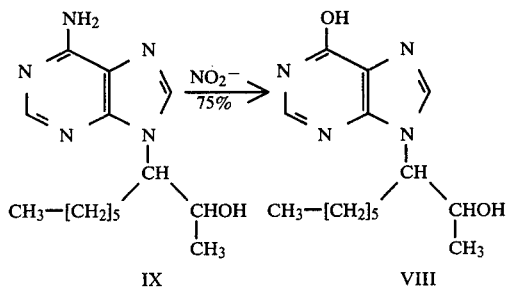

3-ACETAMIDONONAN-2-ONE (II)

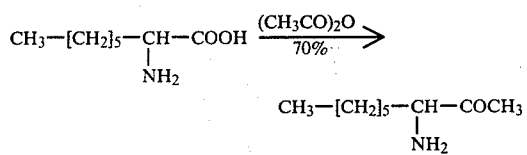

A mixture of 2-amino-1-octanoic acid (I, 200 g, 1.26 mole) in acetic anhydride (960 ml), and pyridine (640 ml) was heated on a boiling water bath for 4 hr. The reaction mixture was evaporated in vacuo, and the residue was partitioned 6-8 times between 5% aqueous solution of $NaHCO_3$ (400 ml) and ether (400 ml). The combined ethereal extracts were dried with anhydrous $MgSO_4$ and evaporated to dryness to give crude 3-acetamidononan-2-one, 154 g (70%).

3-AMINO-2-NONANONE HYDROCHLORIDE (III)

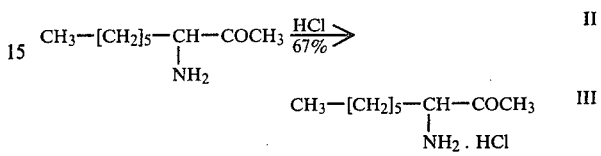

The crude product (II) obtained in the preceding operation (154 g) was dissolved in concentrated aqueous HCl (1,540 ml) and refluxed for 2 hr. and then evaporated to dryness in vacuo. The resulting solid was recrystallized from a warm solution in EtOH (200 ml) and then cooled to 25°. To this solution ether (600 ml) was added. A white crystalline precipitate appears; the suspension is kept at 5° overnight. The precipitate is collected and washed with ether (once with 100 ml) to give 125 g (67%) white crystalline product M.P. 112° dec.

If the crystalline material were not white or had a lower melting point, it should be recrystallized with charcoal from tetrahydrofuran. In one repeat of this procedure there was used 150 ml of hydrofuran for 100 g of the crude hydrochloride (III).

ERYTHRO-3-AMINO-2-NONANOL (IV)

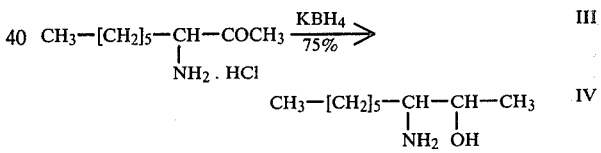

3-Amino-2-nonanol hydrochloride (43.8 g, 0.226 mole) was dissolved in absolute methanol (150 ml) and cooled to −10° in an ice-salt bath. 1/ Potassium borohydride (24.4 g, 0.45 mole) 2/ was added in small portions over a 2-3 hr. period. The mixture is then kept at −10° to −15° for 3 hr. 3,4/ and slowly allowed to reach room temperature (22°), then stirred overnight (20 hr.) at room temperature. The mixture is then evaporated to dryness (syrup) in vacuo and partitioned between $H_2O$ (150 ml) and chloroform (150 ml). The $H_2O$ layer was further extracted (3x) with chloroform (100 ml ea.). The chloroform layer was dried with $MgSO_4$ and evaporated in vacuo to give a slightly yellowish, oily product. This liquid was distilled in high vacuo at 95°–100° (0.15 mm Hg) to give pure erythro-3-amino-2-nonanol, 26.4 g, 75% yield, m.p. 81°–86°.

1. Upon cooling the solution of III, some material precipitates; this has no effect on the outcome of the reaction.
2. At this point, the present procedure differs from that of Schaeffer et al. Schaeffer adds acetic acid at the same time as $KBH_4$, maintaining the pH at 5–6. It has been found that neutralization entails loss of $KBH_4$ and that a pH above 5 is tolerated. More important is the fact that the simultaneous addition of acetic acid and KBH₄ (as proposed by Schaeffer) makes the reaction very difficult to control. The temperature raises considerably and losses in yield and/or quality of the product occur.

3. It is recommended to use an efficient stirring to insure the proper reaction which will be completed when all the small lumps and portions of potassium borohydride have disappeared.
4. Cooling at 0°, as described by Schaeffer et al (Method D, line 4 and ff.) is insufficient. It is an improvement to keep the reaction well below 0°; it is best to keep it below −10° all the time. If the temperature is allowed to go over −10°, substantial loss in yield may result.

ERYTHRO-5-AMINO-4-CHLORO-6-(2-HYDROXY-3-NONYLAMINO)PYRIMIDINE (VI)

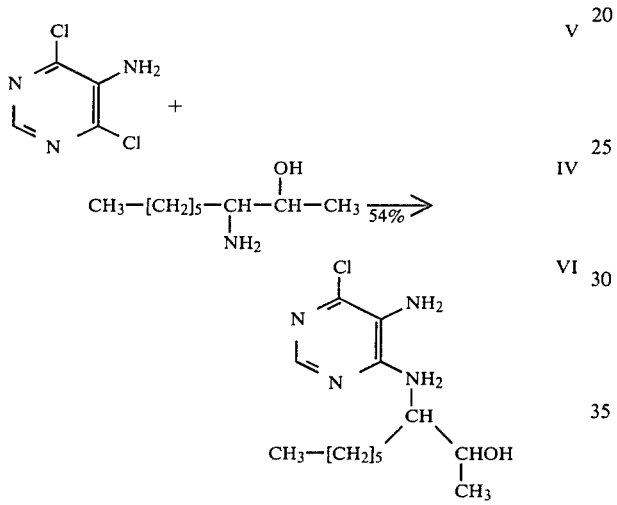

A mixture of 4,6-dichloro-5-aminopyrimidine (V, 24.6, 0.15 mole) and erythro-3-amino-2-nonanol (IV, 26.2 g, 0.164 mole) in 1-pentanol (1.080 ml) and tributylamine (350 ml) was prepared with stirring at 25°. The resulting suspension was heated to reflux under nitrogen atmosphere for 28 hr. (solution took place in about ½ hr.). At that time a sample of the reaction product showed a uv λmax 267 and 297 nm (H₂O, pH 5.5).

The resulting solution was concentrated in a hot water bath at 10 mm pressure to a syrup and further evaporated in an oil bath at 0.1 mm and 100° to yield a viscous liquid to which n-hexane (450 ml) was added. The mixture was refluxed for 1 hr., and the hot, yellowish hexane supernatant was separated from the liquid at the bottom of the round bottom flask.

The resulting light brown oil from which any residual hexane was evaporated in vacuo and dissolved in chloroform (150 ml). This chloroform solution was extracted 8 times with an aqueous saturated solution of NaHCO₃ (250 ml each time). The chloroform layer was then separated, dried (with sodium or magnesium sulfate) and evaporated under high vacuo (0.1 mm) at 40° (water bath) to give a light brown oil which solidified on cooling. This material can be used directly in the next step or purified as follows: The resulting oil was dissolved in 75–100 ml chloroform and n-hexane (ca. 300 ml) added to precipitate out a white crystalline solid which was filtered from the cooled solution. (Extraction is carried out 4–8 times, until carbondioxide is no longer evolved.) This treatment was repeated two more times. Yield: 23.3 g (54%) uv λmax 267, 297 (H₂O, pH 5.5) mp 113°–116°.

ERYTHRO-9-(2-HYDROXY-3-NONYL)6-CHLOROPURINE (VII)

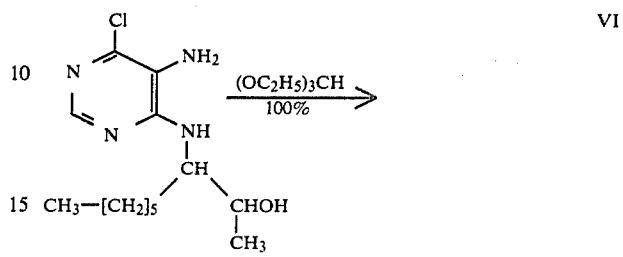

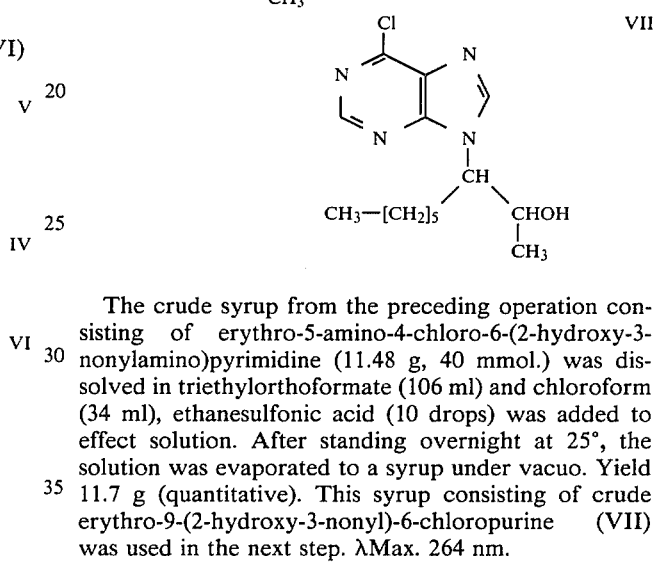

The crude syrup from the preceding operation consisting of erythro-5-amino-4-chloro-6-(2-hydroxy-3-nonylamino)pyrimidine (11.48 g, 40 mmol.) was dissolved in triethylorthoformate (106 ml) and chloroform (34 ml), ethanesulfonic acid (10 drops) was added to effect solution. After standing overnight at 25°, the solution was evaporated to a syrup under vacuo. Yield 11.7 g (quantitative). This syrup consisting of crude erythro-9-(2-hydroxy-3-nonyl)-6-chloropurine (VII) was used in the next step. λMax. 264 nm.

ERYTHRO-9-(2-HYDROXY-3-NONYL)HYPOXANTHINE (VIII)

(By hydrolysis of the 6-chloropurine derivative)

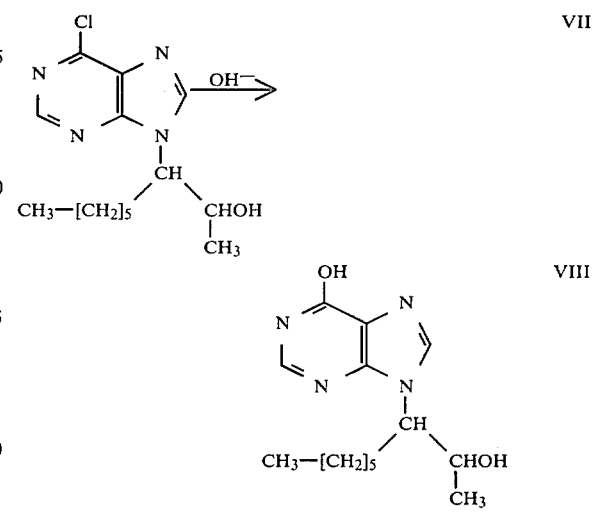

A suspension of erythro-6-chloro-9-(2-hydroxy-3-nonyl)purine (VII, 4.0 g, 13.4 mmol) in 0.5 N NaOH (40 ml) was refluxed for 2 hr. and cooled. Neutralization with glacial acetic acid and cooling gave a crystalline precipitate of erythro-9-(2-hydroxy-3-nonyl)hypoxanthine (VIII) which was filtered and dried. Yield: 3.8 g (quantitative), m.p. 196° uv λmax (pH 5.5) 251 nm.

The crude product (VIII) thus obtained was homogeneous by paper chromatography (3 solvents) and gave negative test for Cl⁻ (copper wire and flame; sodium fusion, acidification and silver nitrate).

Recrystallization of a sample of the crude material 3 times from aqueous ethanol (see Purification) gave colorless crystals. m.p. 202°. Calc. for $C_{14}H_{22}N_4O_2$ (VIII): C, 60.41; H, 7.97; N, 20.13. Found: C, 60.47; H, 7.86; N, 20.08.

PURIFICATION OF ERYTHRO-9-(2-HYDROXY-3-NONYL)HYPOXANTHINE (VIII)

The crude nonyl hypoxanthine (VIII) is purified by recrystallization. The crude material is dissolved by heating in about 6-10 times its weight in ethyl alcohol, and then an equal volume of $H_2O$ is added. The solution is treated with charcoal in an Erlenmeyer and filtered through celite when hot. The solution is evaporated with continuous stirring on a hot plate. Water is added in small portions to replace the evaporated volume until an abundant precipitate appears. Keep on evaporating the solvent to remove all the ethyl alcohol while adding repeatedly $H_2O$ to reach a volume of 8-12 times the weight of material. The loss in material is about 10% per each recrystallization. Two recrystallizations raised the melting point to 202° and gave a colorless crystalline product while the crude material was somewhat yellow or pink and melted at 192°.

ERYTHRO-9-(2-HYDROXY-3-NONYL)-ADENINE. HCl (IX)

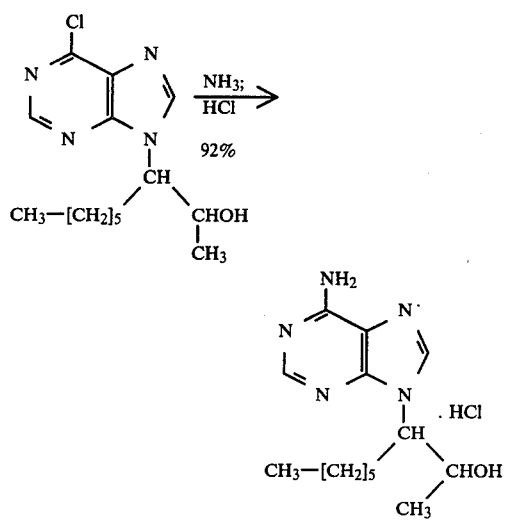

The crude oily erythro-9-(2-hydroxy-3-nonyl)-6-chloropurine (VII) (6.15 g) from the preceding preparations is dissolved in saturated methanolic ammonia (300 ml) and ammonium chloride (1 g) at 80°-100° for 1 hr. in a stainless steel bomb (Parr Instruments). After cooling, the solution was evaporated to dryness in vacuo. Methanol was added and evaporated again (3 times) to eliminate the excess of ammonia.

The syrupy residue was dissolved in absolute methyl alcohol, and dry HCl gas was bubbled, keeping the temperature below 20° (with an ice water bath). After passing HCl for ½ hr., the mixture was cooled at 5°. The precipitate was collected through a sintered glass funnel, washed with cold methyl alcohol and dried in air. Yield 6.0 g (92%) m.p. 173°-175° dec. uv λmax 60 nm (in $H_2O$, pH 5.5).

ALTERNATE ROUTE FOR THE PREPARATION OF ERYTHRO-9-(2-HYDROXY-3-NONYL)HYPOXANTHINE (VIII)

(By deamination of VII)

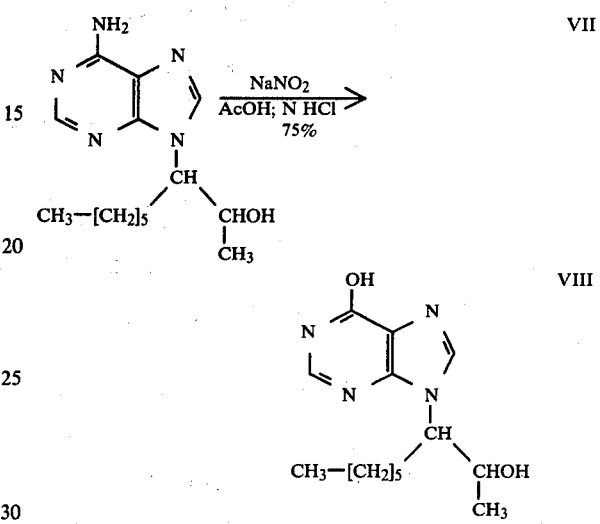

Sodium nitrite (5.6 g, 71 mmole) was added slowly to a solution of erythro-9-(2-hydroxy-3-nonyl) adenine (IX, 4.0 g, 14 mmole) in 50% acetic acid (20 ml) and N HCl (3.2 ml) at 25° with stirring. The mixture was stirred for 2 hr. at 25°. After this time, UV spectrum is monitored. When UV λmax reached 250 mm, the solution was neutralized with 2 N NaOH. The resulting precipitate was filtered and washed with $H_2O$. Yield=3.03 g (75%) m.p.=195°.

An analytical sample was recrystallized (3×) from water yielding a product m.p. 202°. Anal. Calc. for $C_{14}H_{22}N_4O_2$: C, 60.40; H, 7.96; N, 20.13. Found: C, 60.40; H, 7.90; N, 20.12.

Method K

COMPOUND NPT 15426

There was used the procedure of H. J. Schaeffer and S. F. Schwender, J. Med. Chem. 17:6 (1974.)

Method L

PREPARATION OF NPT 15410

0.1 mmoles of 9-(2-hydroxy-3-nonyl)-6-hydroxy purine, NPT 15392 (27.9 mg) and 0.3 mmoles of 2-hydroxypropyl, dimethylammonium 4-(acetylamino)benzoate (DIP.PAcBA) (77.1 mg) were accurately weighed and dissolved in 105 ml of 0.25% sodium carbonate ($NaCO_3$) to yield a 0.1% solution of NPT 15410 (the compound formed from NPT 15392 and (DIP.PAcBA) in a 1:3 molar ratio).

EVIDENCE FOR COMPLEX FORMATION

Phase solubility studies carried out with NPT 15392 and DIP.PAcBA demonstrate that NPT 15392 has increased solubility at increasing concentrations of DIP.PAcBA under conditions of constant pH. This is indicative of an interaction occuring in solution to yield a complex.

In place of the mole ratio of 1:3 (NPT 15392 and DIP.PAcBA), other complexes are formed by using mole ratios of 1:1 and 1:10.

Antiviral activity is shown in Tables 2 and 3.

sorption foci forming units HAFFU) is a quantitative measure of infectivity. The method is as follows.

The monolayers were subcultured in the following manner: The medium was poured off, and the monolayer washed two times with approximately 50 ml per wash of calcium and magnesium free phosphate buff-

TABLE 2
INHIBITION OF INFLUENZA VIRUS REPLICATION BY 9-(HYDROXYALKYL) PURINES

Viral Strain: Influenza A USSR/90($H_1N_1$)

| Test Cpd No. | Compound |  |  |  | % Inhibition of Hemadsorption Foci Conc. (μg/ml) Test Compound |  |  |
|---|---|---|---|---|---|---|---|
|  | $R^1$ | $R^2$ | X | Y | <10 | 10-100 | >100 |
| 15425 | H | H | OH | — | — | — | — |
| 15428 | H | H | OH | DIP . PAcBA | — | — | — |
| 15435 | H | H | SH | — |  | 50 | 10 |
| 15437 | H | H | SH | DIP . PAcBA |  | 65 | 65 |
| 15446 | H | $CH_3$ | OH | — | 2 | 0 | 0 |
| 15447 | H | $CH_3$ | OH | DIP . PAcBA | 10 | 26 | 34 |
| 15431 | H | $CH_3$ | $NH_2$ | — |  | 22 | 0 |
| 15432 | H | $CH_3$ | $NH_2$ | DIP . PAcBA |  | 48 | 62 |
| 15427 | $CH_3$ | H | I | — |  |  |  |
| 15423 | $CH_3$ | H | Cl | — | 2 | 13 | 6 |
| 15433 | $CH_3$ | H | $NH_2$ | — |  | 32 | 0 |
| 15434 | $CH_3$ | H | $NH_2$ | DIP . PAcBA |  | 41 | 62 |
| 15443 | $CH_3$ | H | OH | — |  | 0 | 0 |
| 15444 | $CH_3$ | H | OH | DIP . PAcBA |  | 44 | 54 |
| 15417 | $C_6H_{13}$ | H | OH | — | 18 | 58 | 60 |
| 15418 | $C_6H_{13}$ | H | OH | DIP . PAcBA | 16 | 46 | 52 |
| 15392 | $C_6H_{13}$ | $CH_3$ | OH | — | 86 | 100 | 100 |
| 15410 | $C_6H_{13}$ | $CH_3$ | OH | DIP . PAcBA | 58 | 96 | 96 |
| 15426 | $C_6H_{13}$ | $CH_3$ | $NH_2$ | — | 50 | 96 | 100 |
| 15110 | — | — | — | DIP . PAcBA | 0 | 0 | 20 |

TABLE 3
INHIBITION OF HERPES VIRUS REPLICATION BY 9-(HYDROXYALKYL) PURINES

| NPT No. | Compound |  |  |  | Plaques (PFU) Test (15-150 μg/ml) | Control | Percent Inhibition |
|---|---|---|---|---|---|---|---|
|  | $R^1$ | $R^2$ | X | Y |  |  |  |
| 15392 | $C_6H_{13}$ | $CH_3$ | OH | — |  |  | 98% |
| 15417 | $C_6H_{13}$ | $CH_3$ | OH |  |  |  |  |
| 15418 | $C_6H_{13}$ | H | OH | DIP . PAcBA |  |  |  |
| 15410 | $C_6H_{13}$ | H | OH | DIP . PAcBA |  |  | 98% |

BIOLOGICAL ACTIVITY

Methods

Anti-Influenza Activity—(Hemadsorption Assay)

Upon infection of a monolayer of tissue culture cells by influenza virus, the cell surface is altered so that guinea pig erythrocytes can be adsorbed to the cell surface. The number of foci of adsorbed cells (hemadered saline (PBS), (GIBCO #419) at a pH of 7.2. One ml of trypsin-EDTA solution (GIBCO #530L) containing 0.5 g trypsin (1:250) and 2.0 g EDTA/liter of Modified Puck's Saline A was added at 37° C. to each flask and dispersed over the monolayer with gentle shaking. The flasks were then placed in an incubator at 37° C. for approximately 3–5 minutes depending on the time required to dislodge the cells. Occasional shaking was required. Ten ml of planting medium was added to each flask and the cells dispersed by aspirating and expelling the suspension from the pipette. The contents of a series of flasks were pooled and the cells in the suspension were diluted with planting medium to $7-8.5 \times 10^4$ cells/ml. The planting medium consisted of the following composition: Minimum Essential Medium Eagles (MEM) with Earle's salts and HEPES buffer (GIBCO #236) supplemented by adding the following substances as specified to 87 ml of MEM:

10 ml of fetal calf serum (FCS-GIBCO #614HI)
1 ml of L-glutamine (200 Molar-GIBCO #503)
1 ml of Chlortetracycline (5000 µg/ml) GIBCO #528)
1 ml of 10,000 units penicillin, 10,000 µg streptomycin and 10,000 neomycin mixture (PSN-GIBCO #564)

The cells were subcultured into Linbro tissue culture trays. The trays consisted of 24 flat bottom wells each with a 3 ml capacity per well; the cell culture suspension (1 ml) was added to each wall.

The following day the medium was removed and replaced with fresh planting medium. The monolayers were used for experimentation when they reached a condition in which they were almost confluent (approximately 3-4 days).

When the Linbro tray HeLa cell cultures were ready for experimentation (see cells), the medium was decanted and 1 ml of maintenance medium (MEM with FCS reduced to 3%) containing the compound being tested at a given concentration was added to 4 replicate cultures within a tray.

A series of different drug concentrations ranging from 2.3 to 150 µg/ml were used. Maintenance medium alone was used for control cultures. After the administration of drug and control medium, 0.1 ml of the diluted viral suspension was added to experimental groups and infected control cultures. Saline alone was added to non-infected control cultures. The Linbro trays were then incubated at 37° C. for 18 hours, after which media in all groups was aspirated. Each culture was washed once with PBS. The saline was aspirated and 0.5 ml of a 0.4% v/v guinea pig red blood cell suspension in PBS was added to each culture well. The cultures remained at room temperature for 30 minutes after which the medium was decanted and culture washed 2 times with PBS to remove all but the specifically bound red cells. After the third wash, maintenance medium was added to all cultures.

A Howard Micrometer eyepiece (C8385) was inserted within the ocular of a Nikon inverted phase contrast microscope. Each culture was scanned with a 4×low paper objective and direct counts of hemadsorbed red cells were counted using the eyepiece grid as a field marker. Partial or complete fields were counted per experimental group depending on the resulting number and density of hemadsorbed cells in the infected control cultures. Magnification of 60× or 150× were chosen to obtain the best conditions for enumerating the hemadsorbed cells. Field factors were calculated for counting hemadsorption at 60× and 150×. At 60×magnification, total field count was calculated using a multiplication factor of 55.5. At 150×magnification the multiplication factor was 273. The multiplication factors of 55.5 and 273 represent the total number of fields at 60× and 150×magnifications, respectively. The number of fields counted ranged from 3 to 5 per well with 3 to 4 wells per treatment group employed (see raw data tables in results section for number of fields examined). Means and standard errors were calculated and the data was evaluated using student's t-test analysis.

BIOLOGICAL ACTIVITY

Anti-Herpes Activity—(Plaque Assay)

The infection of tissue culture cells by Herpes virus causes cell lysis. After a period of time these lysed cells are visualized as a tiny clear area (plaque) on a layer of cells. The incorporation of a test substance into the media will reduce the number of plaques if it is capable of preventing virus replication. The method is as follows:

MATERIALS AND METHODS

Virus

There was employed *herpes hominis* type 2 purchased from American Type Culture Collection (ATCC), Bethesda, Maryland, ATCC #VR 540, Lot 3D. The lyophilized viral suspension was reconstituted with 1 ml sterile distilled $H_2O$. The virus was passed twice through HeLa-cell monolayers. The tissue-culture supernates were pooled, dispensed in 1-ml aliquots, and stored at $-70°$ C. The titer of this working-stock suspension was found to be $10^{-4}$ $TCID_{50}/0.1$ ml (2 days' incubation).

Herpes Virus Plaque Assay

Vero cells in log-growth phase were subcultured at a concentration of $1 \times 10^5$ cells/ml in 50-ml Falcon flasks in Eagle's Minimum Essential Medium (MEM), supplemented with 10% fetal calf serum (FCS) and antibiotics. Media were changed the day following planting. The Vero monolayers reached confluence by the second day after planting and with the cells in log phase, the cultures were used for the plaque assay.

Culture media were poured off and the monolayers were wahsed once with phosphate-buffered saline (PBS). Several different dilutions of the working-stock virus suspension were prepared and each culture flask was infected with 0.5 ml of one of the virus dilutions added to FCS-free medium. This medium contained drug at a concentration of 150 µg/ml. Controls were prepared with medium devoid of drug.

Virus adsorption was allowed to proceed for 2 hours at 37° C., during which time the cultures were rocked gently every 15 minutes. Then Media were poured off and the monolayers were washed once with 10 ml PBS.

Agarose was prepared at a concentration of 6% w/v in 50 ml PBS. A stock medium of MEM supplemented with 2% FCS was prepared. Drug was added to some of the stock medium at 150 µg/ml. The three solutions were maintained at 47° C. In addition, a 1:10 dilution of pooled human anti-herpes sera was readied. Just before the start of treatment, 15 ml of the agarose solution were added to 85 ml of medium. Another 15 ml of agarose were added to 85 ml of drug-medium.

Each of the washed monolayers in one group of experiments was treated either with 5 ml of agarose-medium or with 5 ml of agarose-drug-medium. In another group of experiments, each monolayer was treated either with 0.2 ml of anti-herpes sera in 5 ml of stock medium, or with 0.2 ml of anti-herpes sera in 5 ml of drug-medium. The anti-herpes sera were used in place of agarose to localize plaques by neutralizing any free virus in the medium. The flasks were allowed to remain at room temperature for 5 minutes, after which they were incubated at 37° C. for 2 days. Triplicate cultures were used for most treatment groups.

Ten ml of PBS then were added to each flask. Overlays were shaken gently and then were poured out of the flasks. The monolayers were stained with a solution 0.5% w/v crystal violet in 50% methanol in triple-distilled $H_2O$.

Plaques were counted either directly by transmitted fluorescent light and macroviewing, or by the use of light microscopy for microplaques. Microplaques were counted by averaging three fields per experimental group under 150×magnification.

In other tests of antiviral activity the following results were obtained:

| Compound | % Inhibition at μg/ml | | | | Virus |
|---|---|---|---|---|---|
| | 0.1-1.0 | 1.0-10 | 10-100 | >100 | |

Table 3a
INHIBITION OF INFLUENZA VIRUS REPLICATION BY NPT 15410

| Virus | Concentration Range (μg/ml) | | | |
|---|---|---|---|---|
| | .01-1.0 | 1.0-10.0 | 10.0-100 | >100 |
| A/Swine/76 ($H_{lsw}N_1$) | +++[a] | ++ | ++++ | +++ |
| A/Texas/77 ($H_3N_2$) | ++ | + | ++++ | +++ |
| A/Dunedin/73 ($H_3N_2$) | NT | NT | ± | ++ |
| A/Jap/305 ($H_2N_2$) | NT | NT | ++++ | ++++ |
| A/PR8 ($H_0N_1$) | ++ | ++ | ++++ | +++ |
| $A_2$ Hong Kong ($H_2N_2$) | NT | NT | ++ | +++ |

[a] NT = Not tested
± = 10-20% Inhibition
+ = 20-30% Inhibition
++ = 30-50% Inhibition
+++ = 50-70% Inhibition
++++ = >70% Inhibition Immunomodulation activity is shown in Table 4.

Table 4
MODULATION OF CELL MEDIATED IMMUNITY BY 9-(HYDROXYALKYL) PURINES

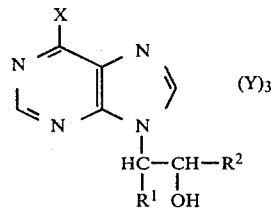

| | Compound | | | | Maximum Percent Change | | | | | | | | |
|---|---|---|---|---|---|---|---|---|---|---|---|---|---|
| | | | | | Mitogen Induced (Con A) Mouse Lymph. Prolif. | | | Mitogen Induced (PHA) Human Lymph. Prolif. | | | Lymphokine Induced (MMF) Guinea Pig Mac. Prolif. | | |
| NPT No. | $R^1$ | $R^2$ | X | Y | .01-1.0 | 1.0-10 | 10-100 | .01-1.0 | 1.0-10 | 10-100 | .01-1.0 | 1.0-10 | 10-100 |
| 15425 | H | H | OH | — | 11 | 0 | | 100 | 0 | 0 | | | |
| 15428 | H | H | OH | DIP . PAcBA | | | | 55 | 45 | −50 | | | |
| 15435 | H | H | SH | — | | | | | | | | | |
| 15437 | H | H | SH | DIP . PAcBA | | | | | | | | | |
| 15446 | H | $CH_3$ | OH | — | 6 | 12 | 0 | 0 | 0 | 0 | 0 | 0 | 0 |
| 15447 | H | $CH_3$ | OH | DIP . PAcBA | | | | | | | | | |
| 15431 | H | $CH_3$ | $NH_2$ | — | −15 | −27 | −47 | 0 | 0 | 0 | | | |
| 15432 | H | $CH_3$ | $NH_2$ | DIP . PAcBA | | | | | | | | | |
| 15427 | $CH_3$ | H | I | — | | | | | | | | | |
| 15423 | $CH_3$ | H | CL | — | | | | | | | | | |
| 15433 | $CH_3$ | H | $NH_2$ | — | +15 | −23 | −65 | 53 | 0 | −50 | | | |
| 15434 | $CH_3$ | H | $NH_2$ | DIP . PAcBA | | | | | | | | | |
| 15443 | $CH_3$ | H | OH | — | +17 | +27 | +27 | 0 | +13 | 0 | +20 | 0 | |
| 15444 | $CH_3$ | H | OH | DIP . PAcBA | | | | | | | | | |
| 15417 | $C_6H_{13}$ | H | OH | — | 0 | 0 | 0 | 0 | 0 | −50 | | 13 | −50 |
| 15418 | $C_6H_{13}$ | H | OH | DIP . PAcBA | 41 | 73 | 26 | | | | 12 | 80 | −50 |
| 15392 | $C_6H_{13}$ | $CH_3$ | OH | — | 172 | 162 | −72 | 11-15 | 20 | −50 | 33 | 23 | |
| 15410 | $C_6H_{13}$ | $CH_3$ | OH | DIP . PAcBA | 140 | 40 | 40 | 30-50 | 60 | | 12 | 23 | |
| 15426 | $C_6H_{13}$ | $CH_3$ | $NH_2$ | — | −50 | −85 | −91 | 6 | −41 | | | | |

Several compounds were tested for Mitogen Induced Murine Lymphocyte Proliferation with the following results:

| Compound | % Stimulation at μg/ml | | | |
|---|---|---|---|---|
| | 01-1.0 | 1.0-10 | 10-100 | >100 |
| 15392 | >50% | 30-50% | 30-50% | not tested |
| 15426 | 0 | 0 | 0 | not tested |
| 15410 | >50 | 30-50 | 30-50 | not tested |
| 15417 | 0 | 0 | 0 | 0 |
| 15418 | 20-30 | >50 | 20-30 | not tested |

| 15392 | 30-50 | — | >70 | >70 | Influenza A Swine 1976 ($H_{lsw}$-$N_1$) |
| 15417 | — | 50-70 | >70 | — | Influenza A Swine 1976 ($H_{lsw}$-$N_1$) |
| 15418 | — | — | >70 | >70 | Influenza A Swine 1976 ($H_{lsw}$-$N_1$) |
| 15426 | 20-30 | 30-50 | 50-70 | 50-70 | (Russian) |
| 15410 | 50-70 | 30-50 | >70 | >70 | (Swine) |

Additional antiviral activity tests of Compound NPT 15410 are shown in in Table 3a.

BIOLOGICAL ACTIVITY

Immunomodulating Assay

The following three assay procedures are used to evaluate the ability of the test substances to modulate the activity of several classes of cells in the immune system. In these systems it is possible to identify both immunopotentiating activity (evidence by an enhancement of the parameter examined) as well as immunosuppressant activity (evidenced by an inhibition of the parameter examined).

1. Mitogen-Induced Mouse Spleen Cell Assay

Mouse spleen cells contain a population of both B and T lymphocytes which can be stimulated by a number of foreign substances (e.g., plant mitogens such as Con A) to proliferate. This enhanced proliferation is an indication of enhanced cell mediated immunity. The method below describes the system used to evaluate test substances as immunopotentiators.

MATERIALS

Concanavalin A (Calbiochem, La Jolla, California), Lot #210073, lyophilized in NaCl, was prepared first as a 1% solution and diluted as a 2×concentration for each dilution (0.5, 1.0, 2.5 μg/ml).

Animals

Six to eight week old male Balb/c and C$_3$H inbred mice were obtained from the following sources: Flow Research Animals, Inc., Dublin, Virginia; Charles River Breeding Laboratories, Wilmington, Massachusetts; Laboratory Supply Company, Indianapolis, Indiana; and Lionel Strong Foundation, San Diego, California.

Cells

Three to five mice were sacrificed by cervical dislocation and the spleens aseptically removed. Pooled spleens were minced and teased with sterile forceps; then strained through a double layer of nylon mesh. The cell suspension was washed once with 15 ml of RPMI 1640 supplemented with 5% fetal calf serum and antibiotics. Cells were cultured at a concentration of $10^6$ cells/0.1 ml/well in micro-plates. Cultures were incubated in the presence or absence of mitogen in a humidified atmosphere containing 5% $CO_2$ for 48 hours. The test compound was added to cultures at various concentrations concomitant with mitogen.

Proliferation

Proliferation was assayed by the degree of incorporation of 1.0 μCi of [$^3$H] thymidine over an 18 hour incubation period. Cultures were harvested by a MASH unit (Otto Hiller Co., Madison, Wisconsin) and thymidine incorporation was assayed by liquid scintillation spectrometry. Cultures were performed in triplicate and data are expressed as means plus or minus the standard error of the experimental means. Drug stimulation indices over control values were also calculated and portrayed graphically.

2. Mitrogen Induced Human Peripheral Blood Lymphocytes

A clinical need exists for therapeutic agents to augment the immune response in patients with deficient or depressed immune states, such as exists in viral diseases or cancer. By studying the ability of agents to augment the proliferation of human peripheral blood lymphocytes in response to a foreign substance one can identify agents with immunopotentiating activity in man. The procedure is that just set forth and that also described by Hadden et al., Infect. & Immunity, February, 1976, pages 382–387, especially pages 382–383.

3. The macrophage represents a subpopulation of white blood cells which is an important component of the immune system in control of both cellular and humoral immunity. The assay system described below evaluates the substances studied as potentiators of macrophage function.

Phytohemagglutinin (PHA) (HA-17) was purchased from Burroughs Wellcome. A preparation containing Macrophage Mitogen Factor (MMF) and Macrophage Activating Factor (MAF) was prepared from antigen-stimulated immune lymph node lymphocytes (guinea pig) as previously described by Hadden et al, Nature 257, 483–485 (1975). Partial purification of this preparation by vacuum dialysis and sephadex G-100 column chromatography yielded an active fraction in the range of 35–70,000 daltons exhibiting both mitogenic and activating properties. The active fraction was employed in both the proliferation and activation assays.

Methods

Ficoll-hypaque purified human peripheral blood lymphocytes were prepared and PHA-induced lymphocyte proliferation was assayed by the incorporation of tritiated thymidine as described in Hadden et al., Cell. Immunol. 20, 98–103 (1975). Each compound was analyzed in the presence of suboptimal, optimal and supraoptimal concentrations of PHA (0.001, 0.01, 0.1 units/ml respectively). Paraffin oil-induced guinea pig peritoneal macrophages were prepared and incubated as monolayer culture (>98% pure macrophages). Lymphokine (MMF)-induced proliferation was assayed by the incorporation of tritiated thymidine at 3 and 5 days of culture as described, Hadden et al, Nature 257, 483–485 (1975). Lymphokine (MAF)-induced macrophage activation to kill Listeria monocytogenes following 5 days of culture in the presence or absence of MAF was performed during a 6 hour period as described in Hadden and England, Immunopharmacology, pages 87–100 (Plenum Press, 1977). Phagocytosis was quantitated during a 20-minute exposure to Listeria monocytogenes by counting the number of macrophages containing bacteria and the number of bacteria per phagocytic cell on gram stained monolayers in Lab-tek chambers. Intracellular killing of bacteria was evaluated by counting the number of cells containing bacteria and the number of bacteria/cell 6 hours after the initial 20 minute exposure. Parallel experiments in which macrophages were lysed and intracellular bacteria were cultured confirm the validity of bacterial activity determined by this manner in this system. The drugs were employed in each of the three systems over serial log concentration range in triplicate in the presence and absence of mitogen or lymphokine. Each type of experiment was performed at least three times. Previous experiments indicate a parallelism of response to pharmacologic modulation in the proliferation and achivation assays.

BIOLOGICAL ACTIVITY

Anti-Leukemic Activity (Inhibition of L-1210 Growth)

Leukemic cells isolated from mice bearing the L-1210 tumor are cultured in vitro and their growth can be measured by counting the number of cells in the culture over a period of time. The incorporation of a test substance into the media will prevent the growth of the leukemic cells, an indication of an effective anti-leukemic agent.

$I_{50}$ (concentration of drug inhibiting growth of L-1210) by % for the tested compounds was as follows:

| Compound | Concentration (micrograms/ml) |
|---|---|
| 15392 | 28 |
| 15410 | 54 |
| 15417 | 47 |
| 15418 | 70 |

The assay system used is set forth below.

To Measure Inhibition of Leukemic Cell (L-1210) Growth

Check to see that there is adequate cell growth in the stock cultures. Use cells 48–72 hours after transfers are done.

Weigh out the drugs at 50 times the desired final concentration and made serial dilutions.

Make up the final medium using 500 mls McCoy's 5A medium, 15% fetal calf serum, 5 mls penicillin-streptomycin solution, and 5 mls antibiotic-antimycotic solution and let it stand at room temperature.

Using sterile technique, add 0.1 ml of the drug dilutions to each tube.

Add an appropriate quantity of cells to the prepared medium. After mixing, remove a 0.5 ml sample, place it in a vial containing 9.5 mls of saline, and count it on the Coulter Counter. Multiply the count by 40 to compensate for the 40 fold dilution (0.5 ml into 0.5 ml saline and record the inoculum.

Add 5 mls of cell suspension to each tube. Swirl the bottle every 4 tubes to insure a more uniform distribution of cells.

Tighten the caps and place in the $CO_2$ incubator at 36°–38° for 96 hours.

After 96 hours remove the tubes from the incubator and count the contents of each on the Coulter Counter. Multiply all counts by 40 and average the four counts for each drug dilution. If the count is less than the inoculum, record 100% inhibition. If the count is greater than the average of the eight control counts, record 0% inhibition. For all other counts use the following formula:

$$\frac{\text{Average cells/ml in treated cultures} - \text{inoculum in cells/ml}}{\text{Average cells/ml in control cultures} - \text{inoculum in cells/ml}} \times 100 = \% \text{ Survival}$$

100% − % servival = inhibition of growth due to treatment.

The subject compounds of this invention have been shown to inhibit the replication of a representative sample of both RNA and DNA viruses using standard tissue culture techniques. In the case of the RNA viruses, several strains of influenza virus belonging to both the A and B sub-types were shown to be inhibited, using the hemadsorption technique (Section II, B). The specific compounds found to inhibit influenza virus replication (Type A/USSR 90) are shown in Table 1. Several members of the Series NPT 15392, NPT 15410, NPT 15417, and NPT 15418 were shown to inhibit the replication of at least 4 different strains of influenza virus at concentrations ranging from 1–150 µg/ml.

In addition, several members of the Series, NPT 15410 and 15392, have been shown to inhibit the replication of Herpes Simplex virus, a member of the DNA class of viruses and a virus responsible for severe mucocutaneous lesions in man, along with the fatal Herpes encephalitis. Other members of this class of viruses are responsible for hoof and mouth disease in swine and cattle and infectious rhinotracheitis in cats and kennel cough in dogs. Even concentrations less than 100 µg/ml of NPT 15392 and 15410 were found to reduce plaque formation caused by Herpes Simplex virus to an extent of >90%. Other members of the RNA and DNA class of viruses are shown in Table 5 and are responsible for the diseases specified. Of all the diseases in the world at least 25% are known to be caused by viruses. In addition, a number of viruses have been isolated that are shown to produce tumors. Thus, antiviral agents may be expected to, by themselves, have some antitumor properties.

It is an established fact that many infectious agents, such as viruses (influenza virus, HSV, Friend leukemia virus), bacteria and fungi cause an immune suppressed stated in the host, weakening his defenses to infection by infectious agents. Most other antiviral antimetabolite substances, like AraC, cause a suppression of host immune defense mechanisms, thereby exhibiting potential to lessen the body's own natural defense mechanisms and enhance secondary infection.

An immunopotentiator or immunomodulator is any agent which either restores depressed immune function, or enhances normal immune function, or both. Immune function is defined as the development and expression of humoral (antibody-mediated) immunity, cellular (thymocyte-mediated) immunity, or macrophage and granulocyte mediated resistance. It logically includes agents acting directly on the cells involved in the expression of immune response, or on cellular or molecular mechanisms which, in turn, act to modify the function of cells involved in immune response. Augmentation of immune function may result from the action of an agent to abrogate suppressive mechanisms derived by negative-feedback influences endogenous or exogenous to the immune system. Thus, immune potentiators have diverse mechanisms of action. Despite the diversity of cell site of action and biochemical mechanism of action of immunopotentiators, their applications are essentially the same; that is, to enhance host resistance.

Applications of Immunopotentiators (1) The principal protective function of the immune system relates to resistance to invasion by pathogens, including viruses, rickettsia, mycoplasma, bacteria, fungi, and parasites of all types. Thus, improvement of immune response, particularly when depressed, would calculatedly improve resistance in infection or infestation by any of the above pathogens. An immunopotentiator alone or in combination with anti-infective therapy can be applied to any and all infectious diseases.

(2) A second protective function of the immune system is thought to be resistance to engraftment of foreign tissue, either natural as in the fetal-maternal relationship; or unnatural as performed by the transplant physician. Immunopotentiators can also be used to facilitate rejection of fetal or placental tissues or to modify or induce tolerance to grafts.

(3) A third protective function of the immune system is thought to be resistance to malignant cell development as in cancer. The use of immunopotentiators can be used in cancer treatment to enhance tumor rejection and to inhibit tumor recurrences following other forms of therapy.

(4) A fourth protective function involves the capacity to recognize foreign-ness and to maintain non-reactivity to self by positive suppressor mechanisms. In autoimmune and related disorders, immune reactivity directed at self antigens or exaggerated, elevated responses are apparent which are self-destructive. Immunopotentiators can be used to restore normal suppressor mechanisms, induce tolerance, or otherwise promote a normal immune response.

Each of the protective functions of the immune system can be modified by non-specific therapy with immunopotentiators alone or in combination with other agents employed to improve resistance or to kill the invading pathogen. In addition, specific resistance can be augmented by use of immunopotentiators in conjunction with some form of antigen as in a vaccine employing, for example, virus, tumor cell, etc. This use can be to induce either specific immunity or tolerance. The latter might be exemplified by use with antigen in allergy or auto-immune diseases. Use of immunopotentiators may be either therapeutic or prophylactic; the latter particularly in aging, where infection, auto-immunity, and cancer are more common. The timing of administration and routes are variable and may be critical in determining whether a positive or negative response results. Any agent capable of augmenting immune response may inhibit it depending on timing and dose; thus, under certain circumstances an immunopotentiator could be used as an immunosuppressive agent for use in allergy, auto-immunity and transplantation.

Table 4 above presents the results of an evaluation of a number of these subject compounds as potentiators of the immune response. Three different test systems were used. The first involves a measure of the ability of the test compound to enhance the ability of mouse lymphocytes to proliferate in response to a plant mitogen (Con A). The second involves measuring the ability of the test compounds to enhance human lymphocyte proliferation in response to a second plant mitogen (PHA). The third system measures the ability of these test substances to enhance macrophage proliferation in response to a natural lymphokine (MMF, Macrophage Mitogenic Factor). This latter response, the proliferation and activation of macrophages, has been shown to be involved in the killing of bacteria, viruses and tumor cells by this class of white blood cells.

Specificant potentiation of the immune response has been observed by 15392, 15410, and 15418.

Finally, the activity of several of these agents, NPT 15392 and 15410 as inhibitors of the growth of abnormal lymphocytes has been determined. Notably, both substances are capable of inhibiting the proliferation of mouse leukemic lymphocytes (an L-1210 cell line) in tissue culture. A 50% inhibition of L-1210 cells was effected by NPT 15392 at 28 μg/ml and by NPT 15410 at 54 μg/ml. The ability to inhibit leukemic lymphocytes at concentrations that stimulate normal lymphocytes is a unique property not known to be present in any other class of substances.

The products of the present invention are members of a class of substances, which specifically inhibit the replication of RNA and DNA virus, modulate (potentiate) the immune response and inhibit the growth of leukemic lymphocytes. Based on in vitro experiments, which demonstrate activity over a concentration range of 0.01–150 μg/ml, dose ranges effective in mammals are 0.05–500 mg/kg. A lack of toxicity has been noted at levels of 1,500 mg/kg in mice for certain numbers of this series.

The immunopotentiators of the invention can be employed, for example, to provide resistance to invasion by the viruses in Table 5.

Table 5

| Virus | Class | Disease |
| --- | --- | --- |
| Arenavirus | RNA | Rift Valley Fever |
| Influenza | RNA | Influenza |
| Rhinovirus | RNA | Common Cold |
| Poliovirus | RNA | Polio |
| Measles | RNA | Rubella |
| Newcastles Disease Virus | RNA | Newcastles disease |
| Rotavirus | RNA | Gastroenteritis in infants |
| Hepatitis Type A | RNA | Infectious Hepatitis |
| Rabies virus | RNA | Rabies |
| Arbovirus | RNA | Encephalitis |
| Vaccinia virus | DNA | Smallpox |
| Herpes Simplex Virus | DNA | Cold sore, Encephalitis, Venereal Disease |
| Herpes Zoster | DNA | Shingles |
| Varicella Zoster | DNA | Chicken pox |
| Adenovirus | DNA | Respiratory |
| Hepatitus Type B | DNA | Chronic Hepatitis, Severe Hepatitis |
| Hoof and Mouth Disease virus | DNA | Hoof and Mouth Disease |
| Machupo Virus | | Hemorrhagic Fever |

POTENTIATION BY DIP.PAcBA OF BIOLOGICAL ACTIVITIES

Of the substances described in Table 1, NPT 15392 and NPT 15446 are new compounds claimed in the application of Alfredo Giner-Sorolla filed on even date. Also new are the DIP.PAcBA salts presented in this table, namely, 15428, 15437, 15447, 15432, 15434, 15444, 15418 and 15410. NPT 15392, NPT 15417, NPT 15426 have all been shown to have significant anti-influenza activity by themselves. In one instance (with NPT 15392) the addition of DIP.PAcBA salt to NPT 15392 to form 15410 does not potentiate the anti-influenza activity. In the case of NPT 15417, addition of DIP.PAcBA salt to form 15418 does potentiate the anti-influenza activity. A summary of the relative ability of DIP.PAcBA salts to potentiate the different biological activities is set forth below.

Table 6

| Compound | Dip . PAcBA Salt | Anti-Influenza | Potentiation Anti-Leukemia | Immuno-potentiation |
| --- | --- | --- | --- | --- |
| 15392 | 15410 | Both are equally active | Yes | Yes |
| 15417 | 15418 | Yes | — | Yes |
| 15435 | 15437 | Yes | — | — |
| 15446 | 15447 | Yes | — | — |
| 15431 | 15432 | Yes | — | — |
| 15433 | 15434 | Yes | — | — |
| 15443 | 15444 | Yes | — | — |

FORMULATIONS

The compounds of the present invention can be fed to a mammal at a dosage of 1–1000 mg/kg of body weight and are believed to be active at levels as low as 0.05 mg/kg. The $LD_{50}$ as determined in mice of NPT 15410 given intraparenterally was 4,300 mg/kg, while subcutaneously was 4,900 mg/kg. NPT 15392 has been given to mice at doses of 1000 mg/kg and no drug related mortality was noted.

They can be administered in tablet or capsule form to humans and where solubility permits in the form of syrups or injectable solutions or where insoluble as suspensions. Typical pharmaceutical formulations are described below:

Capsule:
NPT 15392: 50–500 mg.
Avicel pH 101 (microcrystalline cellulose): to make 800 mg.

Suspension:
Aqueous suspensions can be made with a number of suspending agents incorporated with the active drug substances. Included as suspending agents are such substances as sodium carboxymethylcellulose, Na alginate, gum tragacanth, Avicel RC-591 (microcellulose), methylcellulose, Veegum, Xanthan gum. In addition to a suspending agent such substances as sweeteners, flavors, colorants, preservatives, protective colloids and dispersants may be added.

| TABLET FORMULATION | |
|---|---|
| NPT 15392 | 50–500 mg |
| Avicel pH 101 | 130 mg |
| Starch, modified | 20 mg |
| Magnesium stearate U.S.P. | 5.5 mg |
| Polyvinylpyrrolidone | 22 mg |
| Stearic acid U.S.P. | 30 mg |

| SYRUP FORMULATION | | |
|---|---|---|
| NPT 15392 | 25–125 mg | (or at maximum level of solubility) |
| Corn Sugar | 3.25 g. | |
| Distilled Water | .05 g. | |
| FD and C Red 40 | .00175 g. | |
| Sodium Saccharin | .00250 g. | |
| Alcohol U.S.P. | .08 g. | |
| Methyl paraben U.S.P. | .005 g. | |
| Propyl paraben U.S.P. | .001 g. | |
| Glycerin | .31225 g. | |
| Cherry flavor | .00825 g. | |
| Fruit flavor | .00825 g. | |
| Distilled water g.s.ad | 5 ml. | |

IN VIVO TREATMENT OF MICE WITH NPT 15392 AND NPT 15410: EFFECT ON THE IN VITRO STIMULATION OF SPLEEN CELL PROLIFERATION BY CONCANAVALIN A

The purpose of this study was to determine the effects of in vivo treatment of mice with the compounds NPT 15392 and 15410 on the subsequent activity of spleen cells isolated from these animals and evaluated in vitro for their proliferative response to the mitogen, Concanavalin A (Con A).

PROCEDURE

In Vivo Treatment

Nine male Balb/C mice, 8–9 weeks old, weighing 18–20 gms were divided into three groups. One group was treated twice daily (for 1 day), in the morning and afternoon, with an oral dose of NPT 15392 at 10 mg/kg. The second group was similarly treated with NPT 15410 at 20 mg/kg. A third group, dosed with saline served as a placebo control.

In Vitro Spleen Cell Assay: Cell Preparation

The following day, each group was sacrificed and the spleens removed and pooled. The spleens were minced and the cells washed in RPMI-1640 medium (Grand Island Biologicals) supplemental with 2 mm glutamine and antibiotics. The cell concentration of each preparation was determined by a Coulter counter and adjusted to $5 \times 10^6$ cells/ml with RPMI medium.

Microtiter Plate Assay

Microtiter assays were carried out in 0.2 ml incubations, containing $5 \times 10^5$ cells and Con A or Con A and compounds at the indicated concentrations. All assays were performed with 6 replicates and compared with a blank assay containing only cells. The assay plates were incubated at 37° in 5% $CO_2$ for 4 days. During the final 18–20 hours of incubation, 0.5 ml of $^3$HTdR (10 µCi/ml, 6 $C_i$/m mole) were added to each culture. The cultures were harvested with a multiple automatic sample harvester (MASH) unit and the incorporated $^3$HTdR determined with a Beckman LS 8000 liquid scintillation counter, as a measure of cell proliferation. The results are tabulated as the ratio of the activity in the Con A or Con A and compound treated cultures to the blank cultures.

In vivo treatment with either compound 15392 or 15410 increases the subsequent response of the spleen cells, in vitro, to Con A stimulation at a suboptimal mitogen concentration (5 µg/ml. Thus compound 15410 increased the stimulation ratio to 100:1 compared to 55:1 with the placebo. No significant differences are obtained with either compound 15392 or 15410 treatment when the cells are stimulated with a more optimal concentration of Con A (10 µg/ml).

There was also tested the effect of subsequent in vitro treatment of Con A stimulated cells with NPT 15392 and 15410 at 1 µg/ml. Both compounds show a marked ability to augment the Con A stimulation, particularly at the suboptimal mitogen conecntration (5 µg/ml) and to a lesser extent at 10 µg/ml. At 5 µg/l of Con A, the stimulation by NPT 15392 is 2.8 fold over Con A alone, while that for NPT 15410 is 3.3 fold.

These results indicate an immunomodulating effect of these compounds on spleen cell proliferation. Pre-treatment of animals with either compounds with sensitize the cells to subsequent mitogenic stimulation while exposure of the cells in vitro to the compounds following mitogenic stimulation will augment the proliferative response particularly under conditions when the response to mitogen alone is low.

What is claimed is:

1. A method of imparting immunomodulating activity, antiviral activity or anti-leukemic activity comprising administering to a mammal an effective amount for such purpose of a compound of the formula

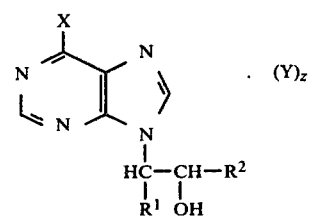

where X is OH, $NH_2$, SH, OR or SR (where R is alkyl of 1 to 4 carbon atoms or benzyl), $R^1$ is H or alkyl of 1 to 8 carbon atoms, $R^2$ is H or methyl, Y is the salt of an amine of the formula

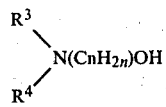

where $R^3$ and $R^4$ are lower alkyl, n is an integer from 2 to 4 and where z is 0 or a number from 1 to 10 with a pharmaceutically acceptable acid.

2. A method according to claim 1 wherein when z is 1 to 10 the acid is p-acetamidobenzoic acid.

3. A method according to claim 2 wherein z is 1 to 10.

4. A method according to claim 3 where $R^1$ is H or n-alkyl of 1 to 8 carbon atoms and $R^3$ and $R^4$ are alkyl of 1 to 4 carbon atoms.

5. A method according to claim 4 where $R^1$ is H or n-alkyl of 1 to 7 carbon atoms.

6. A method according to claim 5 where $R^1$ is H or n-alkyl of 1 to 6 carbon atoms.

7. A method according to claim 6 where $R^1$ is n-hexyl.

8. A method according to claim 3 where X is OH, $NH_2$ or SH.

9. A method according to claim 8 where X is OH.

10. A method according to claim 8 where X is $NH_2$.

11. A method according to claim 8 where X is SH.

12. A method according to claim 3 where $R^2$ is H.

13. A method according to claim 12 where X is OH.

14. A method according to claim 12 were X is $NH_2$.

15. A method according to claim 12 where X is SH.

16. A method according to claim 3 where $R^2$ is methyl.

17. A method according to claim 16 where X is OH.

18. A method according to claim 16 where X is $NH_2$.

19. A method according to claim 16 where X is SH.

20. A method according to claim 4 where X is OH, $NH_2$ or SH and Y is the salt of dimethylaminoisopropanol and p-acetamidobenzoic acid.

21. A method according to claim 20 where X is OH.

22. A method according to claim 20 where $R^2$ is hydrogen.

23. A method according to claim 20 where $R^1$ is n-hexyl.

24. A method according to claim 20 where $R^1$ is methyl.

25. A method according to claim 20 where $R^2$ is methyl.

26. A method according to claim 25 where $R^1$ is n-hexyl.

27. A method according to claim 26 where $R^1$ is methyl.

28. A method according to claim 3 where X is OH, $NH_2$ or SH and $R^1$ is hydrogen.

29. A method according to claim 3 wherein X is OH, $R^1$ is n-hexyl and $R^2$ is methyl.

30. A method according to claim 29 wherein z is 3.

31. A method according to claim 30 where Y is the salt of dimethylaminoisopropanol with p-acetamidobenzoic acid.

32. A method according to claim 29 where Y is the salt of dimethylaminoisopropanol with p-acetamidobenzoic acid.

33. A method according to claim 3 where $R^2$ is H.

34. A method according to claim 3 where X is $NH_2$ and the compound is used in an amount to impart immunoinhibiting activity.

35. A method according to claim 3 where $R^2$ is methyl.

36. A method according to claim 3 wherein the compound is used in an amount to impart immuno-modulating activity.

37. A method according to claim 36 wherein the compound is used in an amount to impart immunostimulating activity.

38. A method according to claim 37 where X is OH.

39. A method according to claim 3 wherein the compound is used in an amount to impart antiviral activity.

40. A method according to claim 39 where X is OH.

41. A method according to claim 3 wherein the compound is used in an amount to impart antileukemic activity, X is OH, $R^1$ is alkyl of 1 to 8 carbon atoms and $R^2$ is methyl.

42. A method according to claim 41 where $R^1$ is n-hexyl.

43. A method according to claim 42 where Y is the salt of dimethylaminoisopropanol with p-acetamidobenzoic acid.

44. A method according to claim 43 wherein the compound is administered to a mammal having leukemia.

45. A method according to claim 36 wherein the compound is used in an amount to impart immunoinhibiting activity.

46. A method according to claim 45 wherein X is OH.

47. A method according to claim 46 where $R^1$ is n-hexyl.

48. A method according to claim 47 where $R^2$ is methyl.

49. A method according to claim 1 where z is 0.

50. A method according to claim 49 where $R^1$ is H or n-alkyl of 1 to 8 carbon atoms and $R^3$ and $R^4$ are alkyl of 1 to 4 carbon atoms.

51. A method according to claim 50 where $R^1$ is H or n-alkyl of 1 to 7 carbon atoms.

52. A method according to claim 51 where $R^1$ is H or n-alkyl of 1 to 6 carbon atoms.

53. A method according to claim 52 where $R^1$ is n-hexyl.

54. A method according to claim 49 where X is OH, $NH_2$ or SH.

55. A method according to claim 54 where X is OH.

56. A method according to claim 54 where X is $NH_2$.

57. A method according to claim 54 where X is SH.

58. A method according to claim 54 where $R^2$ is H.

59. A method according to claim 58 where X is OH.

60. A method according to claim 58 where X is $NH_2$.

61. A method according to claim 58 where X is SH.

62. A method according to claim 54 where $R^2$ is methyl.

63. A method according to claim 62 where X is OH.

64. A method according to claim 62 where X is $NH_2$.

65. A method according to claim 62 where X is SH.

66. A method according to claim 49 where X is OH, $NH_2$ or SH and $R^1$ is hydrogen.

67. A method according to claim 66 where X is OH.

68. A method according to claim 49 where X is OH, $R^1$ is n-hexyl and $R^2$ is methyl.

69. A method according to claim 49 wherein the compound is used in an amount to impart immunomodulating activity.

70. A method according to claim 69 wherein X is $NH_2$ and the compound is used in an amount to impart immunoinhibitory activity.

71. A method according to claim 69 wherein the compound is used in an amount to impart immunostimulating activity.

72. A method according to claim 71 where X is OH.

73. A method according to claim 72 where $R^2$ is methyl.

74. A method according to claim 73 where $R^1$ is 1 to 6 carbon atoms n-alkyl.

75. A method according to claim 74 where $R^1$ is n-hexyl.

76. A method according to claim 69 wherein the compound is used in an amount to impart immunoinhibiting activity.

77. A method according to claim 76 where X is OH.

78. A method according to claim 77 where $R^1$ is n-hexyl.

79. a method according to claim 76 where $R^2$ is methyl.

80. A method according to claim 49 wherein the compound is used in an amount to impart antiviral activity.

81. A method according to claim 80 where X is OH.

82. A method according to claim 81 where $R^2$ is methyl.

83. A method according to claim 82 where $R^1$ is n-hexyl.

84. A method according to claim 49 wherein the compound is used in an amount to impart anti-leukemic activity, X is OH, $R^1$ is alkyl of 1 to 8 carbon atoms and $R^2$ is methyl.

85. A method according to claim 84 where $R^1$ is n-hexyl.

86. A method according to claim 85 wherein the compound is administered to a mammal having leukemia.

87. A method according to claim 1 wherein when the activity is antiviral the virus is influenza virus or herpes virus.

88. A method according to claim 39 wherein the virus is influenza virus or herpes virus.

89. A method according to claim 88 where X is OH.

90. A method according to claim 80 wherein the virus is influenza virus or herpes virus.

91. A method according to claim 90 where X is OH.

92. A method according to claim 91 wherein $R^2$ is methyl.

93. A method according to claim 92 wherein $R^1$ is n-hexyl.

* * * * *